Figure 1:
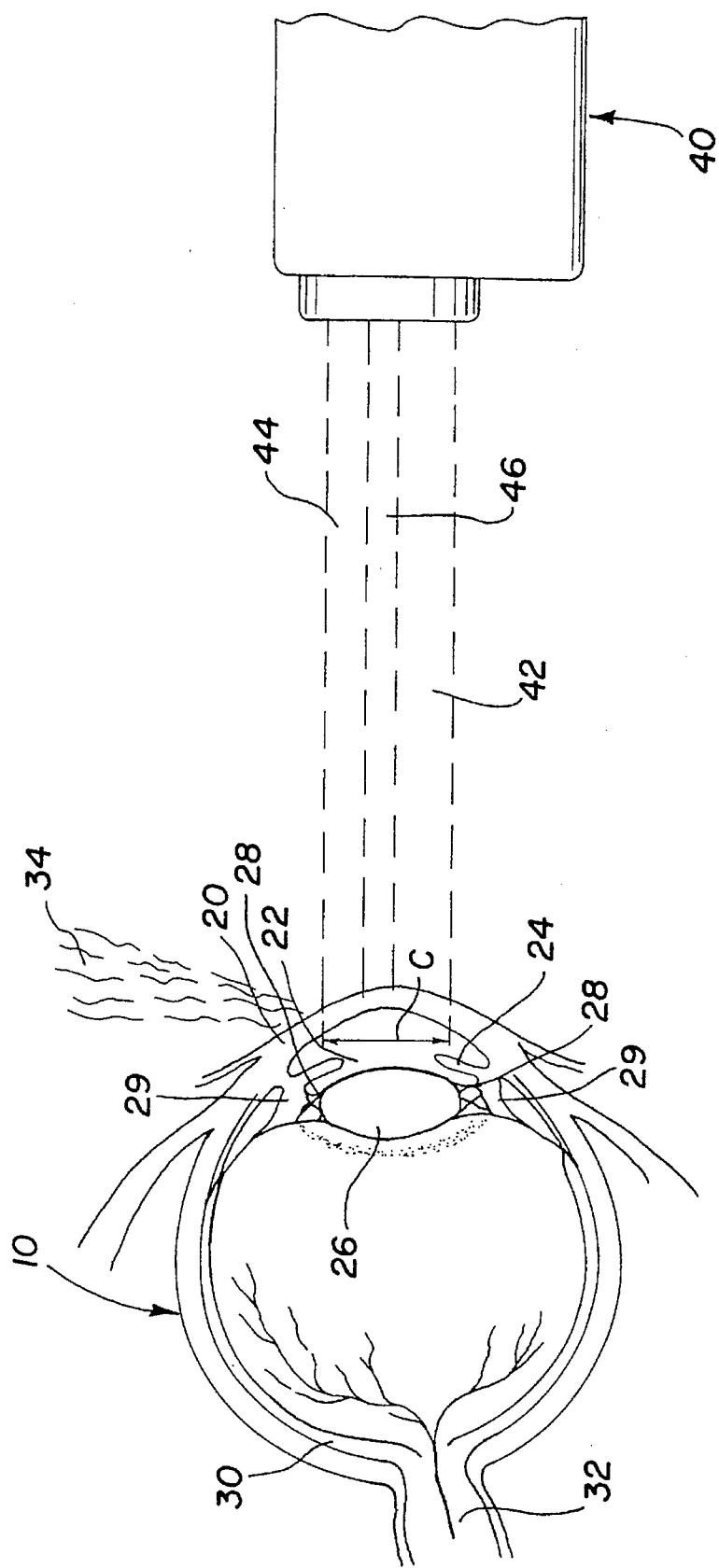

United States Patent [19]
Johnson

[11] Patent Number: 5,603,709
[45] Date of Patent: Feb. 18, 1997

[54] OPTICAL REFRACTION CORRECTION METHODS

[76] Inventor: Donald G. Johnson, 12101 Sullivan Street, Surrey, British Columbia, Canada, V4A 3B1

[21] Appl. No.: 584,888

[22] Filed: Jan. 11, 1996

[51] Int. Cl.$^6$ ............... A61B 17/00; A61N 5/06
[52] U.S. Cl. ................................................. 606/5
[58] Field of Search .................. 606/4, 5, 6, 10, 606/11, 12

[56] References Cited

U.S. PATENT DOCUMENTS

| | | | |
|---|---|---|---|
| 4,732,148 | 3/1988 | L'Esperance, Jr. ............... | 606/5 |
| 4,941,093 | 7/1990 | Marshall et al. ................ | 606/5 X |
| 5,279,298 | 1/1994 | Flower ........................... | 606/4 |
| 5,395,356 | 3/1995 | King et al. ..................... | 606/4 |
| 5,505,723 | 4/1996 | Muller ........................... | 606/3 |
| 5,505,724 | 4/1996 | Steinert ......................... | 606/12 |

*Primary Examiner*—Angela D. Sykes
*Assistant Examiner*—Sonya Harris-Ogugua
*Attorney, Agent, or Firm*—Jack A. Kanz

[57] ABSTRACT

Laser energy is used to remove all the epithelium from a defined treatment zone on the surface of the cornea by focusing a laser beam on the epithelium and monitoring the vapor produced by ablation of the epithelium. The stroma is then sculpted to provide the desired refractive correction by dividing the ablation zone into a set of sub-zones and applying laser energy to each sub-zone in sufficient intensity for predetermined times to remove and reshape the surface of the stroma.

7 Claims, 2 Drawing Sheets

OPTICAL REFRACTION CORRECTION METHODS

This invention relates to a photorefractive correction surgery. More particularly, it relates to methods of removing the epithelium from a defined portion of the cornea and shaping the cornea with controlled laser energy to provide photorefractive correction.

The cornea and lens of an eye act in unison on light entering the eye to focus on the retina. When the refractive power of the cornea and lens are not in proper proportion to the length of the eye, a sharp image is not focused on the retina. Myopia (nearsightedness) is the result of blurred images caused when the focal point of the image is located before the retina. Hyperopia (farsightedness) is the result of blurred images caused when the focal point of the image is behind the retina. Conventionally, corrective lens positioned before the eye (common eyeglasses) are used to correct many common refractive deficiencies. Various surgical procedures have also been developed to effect optical refractive correction. All involve reshaping the cornea to ensure that light passing through the cornea is properly focused on the retina. The cornea is chosen for modification because it is the strongest refracting component of the eye and is accessible without intraocular surgery. The lens has a variable refractive power which accomplishes fine focusing of the image on the retina. This variable power is made possible because the lens is suspended from zonular fibers attached to the ciliary muscles within the eye. A muscular tug on the fibers reshapes the lens.

Conventional radial keratotomy can achieve some results of corrective lenses by flattening the cornea to change the surface shape and thus the refractive power of the eye. Radial keratotomy procedures involve forming precisely placed microscopic incisions in the cornea with a scalpel to change the surface curvature of the cornea. To determine number, placement, size, etc., of incisions, eye surgeons use a computer program implementing a nomogram. A common example of such a nomogram is the Fyodorov nomogram found in the appendix of "Understanding Radial Keratotomy", Ronald A. Schachar, et al. (LAL Pub. 1981), incorporated herein by reference. Nomograms are typically implemented as specialized computer algorithms to provide guidelines for determining the number, depth, length and position of corneal incisions.

Unfortunately, conventional keratotomy procedures may produce undesirable complications such as a starburst effect or glare caused by refraction through the incisions at night from point light sources such as automobile headlights, etc. This effect is usually present immediately following surgery. As the cornea heals and the edema (fluid) leaves the incisions, the effect diminishes.

Laser surgery for refractive correction is an advancement over conventional keratotomy procedures. Instead of incisions, a laser beam is used to selectively remove tissue by vaporization and thereby sculpt or reshape the cornea to conform to a desired shape. Corrective surgery using lasers also relies on specialized algorithms to precisely control the laser beam. However, the epithelium must first be removed to expose the stroma of the cornea. Since the epithelium vaporizes at a rate different from that of the stroma, and because the epithelial layer depth varies among eyes, it has heretofore been impossible to accurately determine the depth of penetration of the laser unless the epithelium (in the treatment zone) is totally removed before beginning timed laser pulses for shaping the stroma. A scalpel is ordinarily used to physically scrape the epithelium from the cornea at least to the depth of Bowman's membrane. Alternatively, partial removal of the epithelium to a predetermined depth is accomplished with a laser and removal of the final portion of the epithelium done with a scalpel. Like conventional radial keratotomy, scraping the epithelium is extremely uncomfortable for the patient, painstakingly time intensive and, because of the rough edges resulting from the scraping, slows the healing process. Additionally, lasers presently used to sculpt the cornea create "islands" in the tissue being sculpted because of minute deviations of energy intensity within laser beams. The periphery of the beam typically has a greater intensity than the center of the beam. The difference in intensity causes non-uniform removal of tissue, forming islands of tissue which often prevent proper healing and can produce an irregular corneal outer surface.

A difficulty encountered in present conventional keratotomy procedures utilizing either laser or conventional surgical techniques is the variation in the corneal thickness among normal eyes. Typically, the corneal thickness is measured manually using an ultrasonic pachymeter. After determining corneal thickness, the surgeon marks the optical center of the eye and the size of the optical zone (or ablation zone) which is dictated by the nomogram algorithm in the computer program. Incisions (or selective ablation) are then made in the cornea.

In accordance with the present invention, laser energy is used to measure and remove the total thickness of the epithelium in the ablation zone, thus completely eliminating use of a scalpel. Total removal of the epithelium is monitored optically by monitoring the vapor (quantity and color) produced while vaporizing the epithelium. Since ablation of the epithelium produces a distinctly visible vapor, removal of the epithelium can be determined visually by observing the vapor produced.

Total removal of the epithelium from the treatment zone is accomplished by visual monitoring and a new surface curvature is produced. The curvature change is determined by the depth difference of peripheral epithelium removal and total epithelium removal from the center of the zone. Since Bowman's membrane is relatively thin, it is quite difficult to determine the rate at which it is ablated. For purposes of this disclosure, Bowman's membrane is considered part of the stroma.

Figure 2:
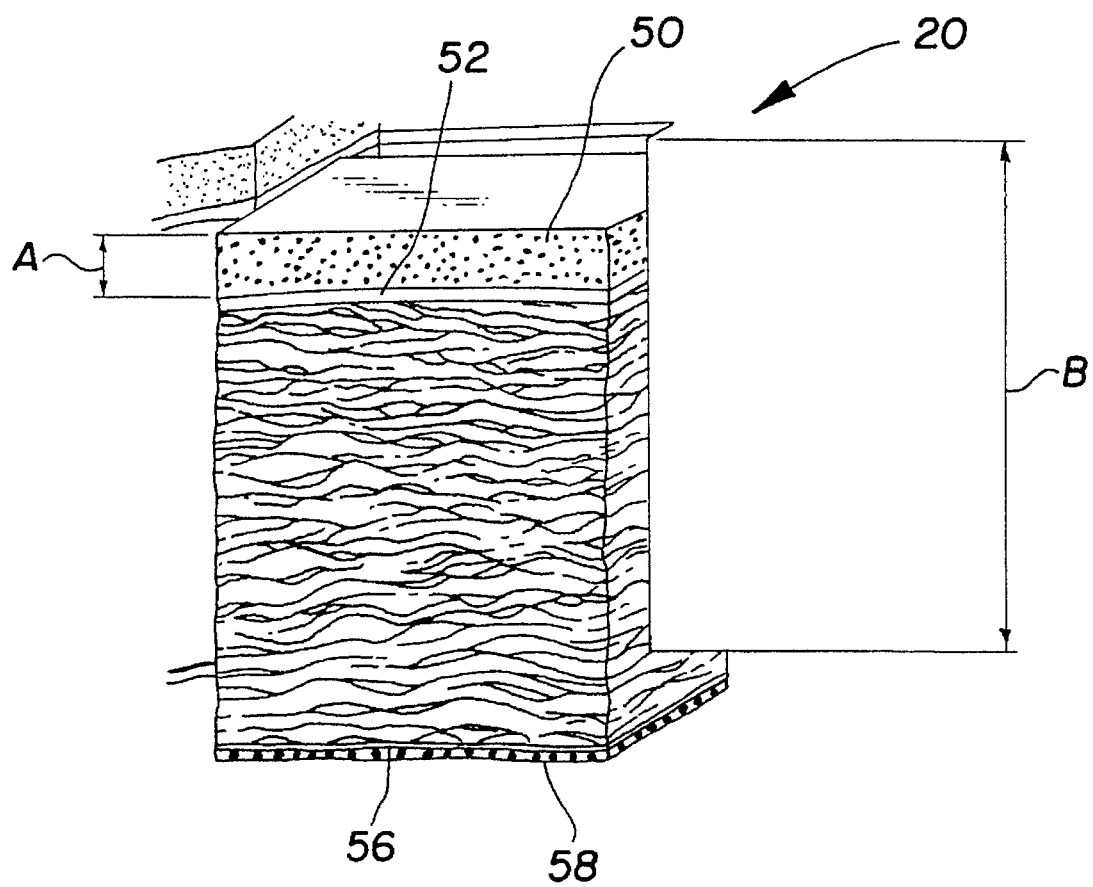

The refractive ablation is based on the new curvature produced by laser removal of the epithelium. For refractive ablation, the treatment zone is divided into multiple zones of incrementally larger diameter (and sometimes multiple passes in the same diameter zone). The combination of total epithelium removal with a laser and use of multiple zone/ multiple pass nomograms developed for the new curvature produced by total epithelial removal addresses and considerably reduces all complications which can occur with photorefractive keratectomy. Using the laser surgery procedures of this invention thus eliminates scarring, etc., commonly associated with the incisions of conventional radial keratotomy. The time required for surgery and healing is reduced and the quality and precision of refractive correction is vastly increased. Obviously, apparatus for practicing the invention and procedures utilizing the invention may take various forms and be suitable for use in a wide variety of surgical procedures. Other features and advantages of the invention will become more readily understood from the following detailed description taken in connection with the appended claims and attached drawing in which:

FIG. 1 is cross-sectional view of an eye with a laser beam applied to the cornea; and FIG. 2 is a exaggerated perspective view, partially in sectional detail, of the layers of the cornea of the eye.

An eye (generally designated by the numeral 10) is illustrated in cross-section in FIG. 1. The cornea 20 forms the outer front portion of the eye 10 covering the pupil 22 which is bordered by the iris 24. A lens 26 is supported behind the iris 24. Zonular fibers 28 connected between the ciliary muscles 29 and the lens 26 provide refined focal manipulation of the lens 26. An optic nerve 32 conveys electrical impulses to the brain representing images formed on the retina 30.

A laser beam generator (referred to as a laser and designated by the numeral 40) directs a beam of energy onto the eye to remove the epithelium 50 by ablation and to sculpt the stroma 54 (illustrated more clearly in FIG. 2). Lasers are preferred over mechanical methods such as scraping to remove corneal tissues such as the epithelium 50 and the stroma 54 because of the degree of precision available with computer-controllable lasers. Furthermore, lasers cream less risk of a decentered (with respect to the pupil 22) treatment zone or ablation zone on the cornea 20.

A suitable laser 40 for corrective eye surgery purposes is an excimer laser. This laser creates an energy beam 42 by passing high voltage electric current through a tube containing gaseous fluorine. Energy in the form of a narrow, uniform light beam is produced which, when directed through an appropriate lens system, causes disruption or vaporization of the corneal tissues. Various other lasers, including solid state and gaseous lasers, which produce collimated beams of energy at the desired wavelengths may also be used.

By controlling the energy, size and shape of the laser beam 42 the surface of cornea 20 can be reshaped so that light passing though the cornea 20 is refracted to a focal point on the retina 30. As the surface of the stroma 54 is reshaped, the refractive power of the cornea 20 is changed. When refractive power is reduced, myopia is reduced. Hyperopia, astigmatic conditions, etc., may also be corrected by selective removal of tissue.

The cross-sectional detail of the cornea 20 of FIG. 2 illustrates the corneal epithelium 50 with Bowman's membrane 52 directly beneath the epithelium 50. Bowman's membrane covers the front side of stroma 54. The inside is covered by Descemet's membrane 56 and an endothelium 58.

Before the stroma 54 can be sculpted, the corneal epithelium 50 must be removed from the ablation zone C. Once the corneal epithelium 50 is removed, multi-pass multi-zone ablation procedures can be applied to reshape the stroma and thereby correct various degrees and types of photorefractive problems such as hyperopia, myopia, astigmatism, etc.

As illustrated in FIG. 2, the epithelium 50 has a uniform epithelial depth or thickness A. However, thickness A may vary from patient to patient. With prior laser eye surgery procedures, measurement of the thickness of the epithelium 50 was desired but not readily obtained. The overall thickness B of the cornea 20 can be determined with an ultrasonic pachymeter, but the thickness A of the epithelium 50 alone could not be readily determined. Since the epithelium and stroma ablate at different rates and the nomogram used for determining time of exposure to the laser beam is based on known uniform removal rates, prior procedures required that the epithelium be removed surgically as by scraping. It has been discovered, however, that total removal of the corneal epithelium 50 may be precisely and accurately performed with a laser beam 42 applied directly to the cornea 20. As the epithelium 50 is ablated, a vapor 34 is generated. The vapor 34 is monitored and a variation in color and/or amount (density) is noted which is indicative of penetration of the peripheral portion of the beam through the epithelium. Vapor disappears upon complete removal of the epithelium 50.

The laser beam 42 is typically applied to the eye as uniformly as possible in a treatment or ablation zone C. Ablation zones typically have a diameter of about six (6) millimeters but can be increased or decreased as desired, depending on the characteristics of the laser 40 used. As the epithelium is ablated, the vapor 34 generated can be monitored visually; with a computer-controlled spectral analysis device; or with any other suitable device which can automate the procedure. The vapor 34 is best monitored visually under a low intensity background light such as a lamp having a conventional incandescent light bulb. When removal of the epithelium 50 is completed, a new surface curvature is produced which produces a refractive change in the eye. The amount of refractive change (diopter power) is not dependent on the thickness of the epithelium 50, but on the difference in depth of penetration of the beam between the point at which the first change in color or intensity is observed (peripheral penetration) and the point at which total disappearance of color occurs (complete removal). For example, if the epithelial depth difference has a mid-twenties value of epithelial depth units, then one diopter curvature change is obtained. If the depth difference is over thirty epithelial depth units, one and one-quarter diopters of power correction is obtained. If the depth difference is under twenty epithelial depth units, then a three-quarter diopter of power correction is obtained. This refractive correction of the eye 10 is taken into consideration before sculpting the stroma 54 and applied to the treatment nomogram to obtain the objective diopter power factor for overall refractive correction.

With the epithelium 50 removed, the stroma 54 is exposed. (Bowman's membrane, as shown in FIG. 2, is considered part of the stroma 54 for purposes of this disclosure.) The stroma is then sculpted to correct the focal point of light entering the eye 10.

General techniques for sculpting the stroma 54 with lasers are known and will not be discussed in detail here. The methods disclosed herein employ multi-zone multi-pass applications of beam 42 of laser energy to the ablation zone C. Multi-zone multi-pass ablation is an improvement over prior laser techniques and results in forming a smoother surface on the stroma 54. The smoother corneal surface promotes and benefits healing without producing haze problems. The number of zones and the number of passes varies for the refractive correction required.

The energy beam 42 produced by conventional lasers 40 has intensity variations from the center portion 46 to the peripheral portion 44. In most cases, the greater power intensity exists in the peripheral portion 44. (In some lasers, the greater power intensity is found in the center of the beam.) Due to this characteristic, islands or dimples may form in the stroma 54 which can (a) cause regression of the eyesight correction, (b) cause formation of a haze on the eye with healing or (c) create risks of irregular astigmatism. In accordance with the invention an ablation process using a multi-zone multi-pass nomogram is utilized to correct for inconsistencies within the laser beam 42 and to avoid or limit the complications listed above.

To utilize the principles of the invention, the ablation zone C is divided into a predetermined set of sub-zones, each having a common center and a different diameter. The laser beam 42 is applied to each zone by starting in the common center and expanding the diameter of the beam to coincide with the diameter of the treatment sub-zone. For example, if the ablation zone C is five (5) mm in diameter, the zone C may be divided into a first sub-zone which is three (3) mm in diameter, a second sub-zone which is four (4) mm in diameter and a third sub-zone which is five (5) mm in diameter. The cornea surface is ablated from each sub-zone in a pass which starts at the center and expands to the diameter of the sub-zone. In the example described above, one pass is made over each sub-zone. The sub-zones are treated with each having a progressively increasing diameter. Each pass starts at center and expands to its determined diameter, always re-treating the previous sub-zone. This ensures adequate central treatment and increased smoothness with each subsequent pass and a properly defined contour to the ablation.

The amount of stroma 54 removed from each pass is determined by the characteristics of the laser as controlled by the nomogram. The order in which each sub-zone is treated is determined by the nomogram to effect the desired reshaping of the stroma. The beam 42 may be passed over the same sub-zone more than once, depending on the dioptic power being treated to remove additional tissue. The intensity and time duration of each pass is predetermined by the nomogram to remove the desired portion of the stroma 54. Multiple passing reduces heat energy build-up in the eye 10 and also promotes a smoother sculpted surface of the stroma 54. Once the desired amount of correction is obtained, no further smoothing is required.

It will be appreciated that the laser beam 42 may be controlled so that multiple passes may be made over any zone and the passes can be overlapped to ensure formation of a smooth surface. By using laser energy to remove the epithelium and progressive multi-zone multi-pass reshaping of the stroma, a very smooth and precisely predictable corneal correction can be achieved. The surface will readily and quickly heal to form a desirably smooth surface because the laser causes less trauma, forms an infinitely smoother surface and leaves no residual debilitated epithelium cells.

Although the invention has been described with particular reference to specific photorefractive correction techniques, the forms of the invention shown and described are to be taken as preferred embodiments which illustrate the principles thereof. Various changes, modifications and rearrangements may be resorted to without departing from the spirit and scope of the invention as defined by the appended claims.

What is claimed:

1. A method of removing the epithelium from a defined area of the corneal surface of an eye comprising:

(a) applying a beam of laser energy to a defined area of corneal surface with sufficient energy intensity to vaporize said surface;

(b) monitoring the vapor produced with time to determine variations in color of vapor produced;

(c) monitoring the vapor produced with time to determine variations in density of vapor produced; and (d) removing said beam from said surface when disappearance of vapor is observed.

2. A method as defined in claim 1 wherein said monitoring is visual and including the step of reducing ambient light below normal while vaporizing said epithelium.

3. A method of reshaping the cornea surface of an eye comprising:

(a) applying a beam of laser energy to a defined area of cornea surface with sufficient energy intensity to vaporize said surface;

(b) monitoring the vapor produced by vaporization of said surface with time to determine variations in color of vapor produced;

(c) monitoring the vapor produced by vaporization of said surface with time to determine variations in density of vapor produced;

(d) determining the difference in depth of penetration of said beam between the point at which the first change in vapor color or change in vapor density is observed and the point at which total disappearance of vapor is observed; and (e) applying the determined difference in depth to the treatment nomogram used for reshaping the stroma.

4. A method as defined in claim 3 including the step of reducing ambient light below normal while vaporizing said epithelium.

5. A method as defined in claim 3 wherein said monitoring is visual.

6. A method of correcting optical refraction in an eye comprising the steps of:

(a) removing the corneal epithelium from the surface of an eye to define an ablation zone on the stroma by vaporizing all the epithelium from the ablation zone with laser energy;

(b) dividing the ablation zone into a set of sub-zones, each of which has a common center and a different diameter;

(c) applying a be am of laser energy to each of said sub-zones with sufficient energy and for sufficient time to remove the surface of the stroma exposed in said sub-zone by beginning at the common center and expanding the beam to the diameter of each said sub-zone; and (d) applying a beam of laser energy to at least one of said sub-zone a second time with sufficient energy and for sufficient time to remove the surface of the stroma exposed in said sub-zone.

7. A method of correcting optical refraction in an eye comprising the steps of:

(a) removing the corneal epithelium from the surface of an eye to define an ablation zone of predetermined dimensions on the surface of the stroma by ablation of all the epithelium in said ablation zone with a laser beam;

(b) dividing the ablation zone into a set of sub-zones, each having a common center and a different diameter;

(c) applying laser energy to each of said sub-zones with sufficient energy and for sufficient time to remove the surface of the stroma exposed in said sub-zone; and (d) applying laser energy to at least one of said sub-zones in a second pass with sufficient energy and for sufficient time to remove the surface of the stroma exposed during said second pass.

* * * * *

UNITED STATES PATENT AND TRADEMARK OFFICE
CERTIFICATE OF CORRECTION

PATENT NO. : 5,603,709
DATED : February 18, 1997
INVENTOR(S) : Donald G. Johnson It is certified that error appears in the above-indentified patent and that said Letters Patent is hereby corrected as shown below:

Col. 3, line 17, "cream" should read ---create---

Col. 5, line 59, "cornea" should read ---corneal---

Col. 6, line 2, "cornea" should read ---corneal---

Col. 6, line 30, "be am" should read ---beam---

Col. 6, line 37, "sub-zone a second time" should read ---sub-zones a second time---

Signed and Sealed this

Twenty-fourth Day of June, 1997

Attest:

BRUCE LEHMAN

Attesting Officer

Commissioner of Patents and Trademarks